(12) United States Patent
Mitchell et al.

(10) Patent No.: US 10,617,846 B2
(45) Date of Patent: Apr. 14, 2020

(54) GUIDEWIRE ADVANCING DEVICE AND METHOD

(71) Applicant: Redsmith, Inc., Walnut Creek, CA (US)

(72) Inventors: James D. Mitchell, Walnut Creek, CA (US); Andrew A. Thoreson, Long Lake, MN (US)

(73) Assignee: Redsmith, Inc., Walnut Creek, CA (US)

( * ) Notice: Subject to any disclaimer, the term of this patent is extended or adjusted under 35 U.S.C. 154(b) by 170 days.

(21) Appl. No.: 15/653,624

(22) Filed: Jul. 19, 2017

(65) Prior Publication Data

US 2018/0021545 A1 Jan. 25, 2018

Related U.S. Application Data

(60) Provisional application No. 62/365,442, filed on Jul. 22, 2016, provisional application No. 62/365,247, filed on Jul. 21, 2016.

(51) Int. Cl.
| | |
|---|---|
| *A61M 25/01* | (2006.01) |
| *A61M 25/06* | (2006.01) |
| *A61M 25/09* | (2006.01) |

(52) U.S. Cl.
CPC .... *A61M 25/0113* (2013.01); *A61M 25/0606* (2013.01); *A61M 25/09041* (2013.01); *A61M 25/065* (2013.01)

(58) Field of Classification Search
CPC .......... A61M 25/0113; A61M 25/0606; A61M 25/09041; A61M 25/09; A61M 25/0905; A61M 5/00; A61M 25/00; A61M 25/0631; A61M 24/0693; A61B 2017/00292; A61B 17/00234; A61B 17/00; A61B 17/34; A61F 2/02; A61F 2/04; A61F 2/06; A61F 2002/041; A61F 2/042; A61F 2002/043; A61F 2002/044; A61F 2002/045; A61F 2002/046; A61F 2002/047; A61F 2002/048; A61F 2002/061; A61F 2/062; A61F 2/064; A61F 2002/065; A61F 2002/068; A61F 2002/067; A61F 2/07; A61F 2002/072; A61F 2002/075; A61F 2002/077; A61F 2/95; A61F 2002/9517; A61F 2/962; A61F 2/958; A61F 2002/9583
See application file for complete search history.

(56) References Cited

U.S. PATENT DOCUMENTS 4,713,059 A * 12/1987 Bickelhaupt ....... A61M 25/0113
242/588.6
4,850,974 A * 7/1989 Bickelhaupt ....... A61M 25/0113
604/171
(Continued)

*Primary Examiner* — Elizabeth Houston
*Assistant Examiner* — David C Eastwood
(74) *Attorney, Agent, or Firm* — FisherBroyles, LLP; Victoria L. Boyd; Rachel Huffstetler

(57) ABSTRACT

The guidewire advancing device and method according to the present invention is used with a tubular catheter body configured to receive a hollow needle for receiving the guidewire. The guidewire advancing device includes the guidewire, guidewire housing, and means for advancing and retracting the guidewire. The means for advancing the guidewire includes a spool assembly or a slide tab and may also include a rack and pinion assembly for translation of forces to advance the guidewire.

29 Claims, 20 Drawing Sheets

(56) References Cited

U.S. PATENT DOCUMENTS

| | | | |
|---|---|---|---|
| 5,159,861 A * | 11/1992 | Anderson | A61B 17/22 226/127 |
| 5,325,746 A * | 7/1994 | Anderson | A61B 17/22 24/115 M |
| 5,524,635 A * | 6/1996 | Uflacker | A61B 17/22012 600/585 |
| 5,579,780 A * | 12/1996 | Zadini | A61M 25/09041 600/585 |
| 5,749,371 A * | 5/1998 | Zadini | A61M 25/09041 600/481 |
| 6,197,001 B1 * | 3/2001 | Wilson | A61M 25/09041 604/157 |
| 6,231,564 B1 * | 5/2001 | Gambale | A61M 25/0113 600/585 |
| 6,551,281 B1 | 4/2003 | Raulerson et al. | |
| 6,626,869 B1 | 9/2003 | Bint | |
| 8,728,035 B2 * | 5/2014 | Warring | A61M 25/0606 604/159 |
| 8,911,487 B2 * | 12/2014 | Bennett | A61M 25/01 623/1.11 |
| 8,932,258 B2 | 1/2015 | Blanchard et al. | |
| 9,050,438 B2 * | 6/2015 | Rollins | A61M 25/09041 |
| 2005/0245847 A1 * | 11/2005 | Schaeffer | A61M 25/09041 600/585 |
| 2007/0016164 A1 * | 1/2007 | Dudney | A61M 25/0136 604/523 |
| 2008/0183206 A1 * | 7/2008 | Batiste | A61F 2/01 606/200 |
| 2010/0318105 A1 * | 12/2010 | Jayant | A61B 17/12013 606/148 |
| 2011/0046553 A1 * | 2/2011 | Nagano | A61B 17/12113 604/156 |
| 2011/0137252 A1 * | 6/2011 | Oster | A61B 17/3415 604/158 |
| 2012/0220942 A1 * | 8/2012 | Hall | A61M 25/0606 604/164.1 |
| 2013/0281787 A1 * | 10/2013 | Avneri | A61M 25/0133 600/208 |
| 2014/0094774 A1 * | 4/2014 | Blanchard | A61M 25/0097 604/506 |
| 2015/0119860 A1 * | 4/2015 | Khalaj | A61M 25/0113 604/528 |
| 2016/0067453 A1 * | 3/2016 | Braithwaite | A61M 25/0631 604/164.08 |
| 2018/0021545 A1 * | 1/2018 | Mitchell | A61M 25/0113 606/108 |
| 2018/0256862 A1 * | 9/2018 | Bagwell | A61M 25/09041 |

* cited by examiner

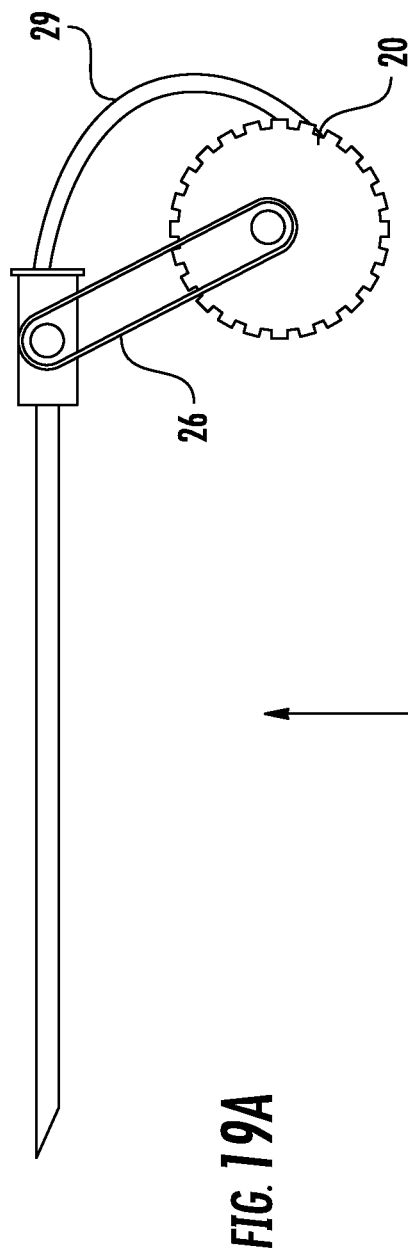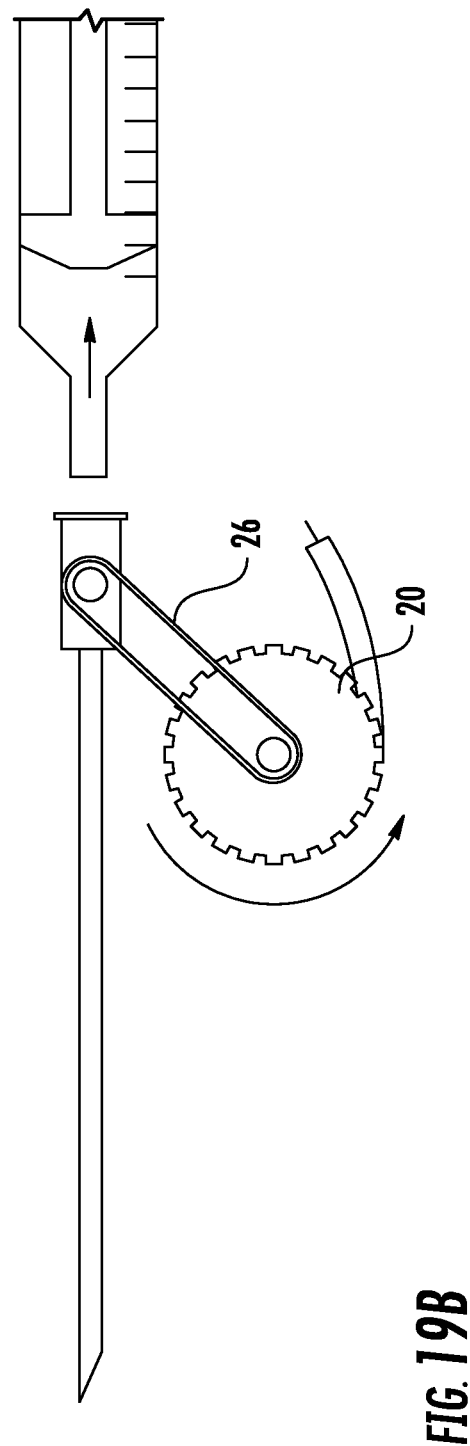
FIG. 19A
FIG. 19B

GUIDEWIRE ADVANCING DEVICE AND METHOD

CROSS-REFERENCE TO RELATED APPLICATIONS

This application is a continuation of, and claims priority to, U.S. Pat. App. No. 62/365,247 filed Jul. 21, 2016, and U.S. Pat. App. No. 62/365,442 filed Jul. 22, 2016, the disclosures of both are incorporated herein by reference.

FIELD OF THE INVENTION

The present invention is directed, generally, to a guidewire advancing device used in connection with medical devices for providing intravascular access into a blood vessel, including veins, arteries, or other anatomical structure for advancing the guidewire used to place such medical devices within the anatomical structure. More specifically, the guidewire advancing device rapidly and easily advances sufficient lengths of wire for rapid and effective intravascular placement of the medical device, such as through the proximal end of an access needle integrated with a catheter or through the proximal end of a needle not integrated with a catheter.

BACKGROUND OF THE INVENTION

Intravascular (IV) access is a mainstay of medical care, and provides a conduit for delivery of life-saving medications, fluids, and nutrition. Furthermore, venous access allows the aspiration and sampling of blood for diagnostic purposes to learn more about the medical patient. IV access may be within a peripheral vein, a central vein, or an intermediate placement such as a peripherally inserted central catheter (PICC) or midline/extended dwell peripheral IV (EDPIV). Intra-arterial access is also commonplace, and the archetype of arterial access is that of the well-described arterial "art" line. Rather than serving as a conduit for the administration of fluids as is seen in venous lines, arterial lines are most frequently employed for diagnostic purposes in the invasive, yet accurate, collection of vital signs and blood gases. Finally, arterial access also enables percutaneous introduction of vascular devices, namely hemostatic sheaths, for the subsequent introduction and exchange of various catheters, wires, and other endovascular devices.

Barriers to effective and safe intravascular access include limitations in patient anatomy, patient medical condition, potential loss of sterility, and user proficiency. Anatomic barriers include size and depth of the vessel, tortuosity or lack of a sufficient inline segment, vessel webs, vessel spasm, and lack of good direct or ultrasound visualization. When patients require intravascular access, they are often in an unhealthy state, which may further complicate the creation of durable access, including smaller vessels in the setting of dehydration or systemic illness, as well as concern for potential bleeding complications in the ill and anticoagulated patient. Additionally, pathologic conditions of the blood vessels exist, which may complicate vessel access. Venous varicosities, and both arterial and venous stenosis and vasospasm, are examples. Finally, sterility may be broken dependent on the preparation and positioning of the patient's access site, but may often be related to operator error while trying to control an unwieldy object, or make multiple device exchanges. All the aforementioned barriers may be further complicated by individual skill and training. Therefore, desirable attributes of a vascular access device include an intuitive device whose components, namely the wire, are user-friendly and sufficiently long enough to extend sufficiently within the vessel to maximize trackability, and ultimately, the technical success, sterility, and safety of introducing an integrated catheter.

SUMMARY OF THE INVENTION

It is, therefore, advantageous to provide a guidewire advancing device for rapidly, efficiently, and effectively advancing the guidewire through a needle for medical device placement within an anatomical structure, such as an artery or vein, while also rendering the procedure as minimally invasive as possible. Indeed, the guidewire advancing device may be single-handedly operated. The guidewire advancing device may be used in conjunction with any medical device employing a guidewire, including U.S. Ser. No. 15/008,628 for Rapid Insertion Integrated Catheter and Method of Using an Integrated Catheter, which is incorporated herein by reference.

The present invention overcomes shortcomings of the prior art by providing a novel guidewire advancing device which facilitates guidewire insertion into a target vessel for gaining vascular access, such as performing an endovascular procedure. The guidewire advancing device according to the present invention is used with a tubular catheter body configured to receive a hollow needle for receiving the guidewire. The guidewire advancing device includes the guidewire, guidewire housing, and means for advancing and retracting the guidewire. The means for advancing the guidewire according to one aspect of the present invention include a spool assembly comprising a spool for receiving the wound guidewire and a pair of discs configured for enabling rotation of the spool to advance the guidewire and for constraining the guidewire during use. The guidewire may be engaged with the needle during use, or it may be pre-assembled with the needle wherein advancement of the guidewire advances the wire distally from the needle tip for intravascular placement. According to another aspect of the present invention, the means for advancing the guidewire includes a generally rectangular housing with a channel defined by an outer surface for receiving a slide tab. The slide tab, on its rear surface within the housing, is connected to a proximal end of the guidewire for urging the guidewire proximally towards an end wall, and then distally so as to advance the guidewire beyond the housing. Another aspect of the present invention includes a rack and pinion assembly to further facilitate translation of forces from the user to the wire advancement and which may be employed with either a spool or sliding tab as the means for interfacing with the user to advance the guidewire. The method of using the device permits the treating clinician to effectively, accurately, and rapidly advance the guidewire for intravascular placement of a medical device. These and other objectives are met by the present invention.

BRIEF DESCRIPTION OF THE DRAWINGS

FIGS. 19A and 19B are schematic representations of the guidewire advancing device of FIGS. 1-7 moveably connected to the needle or catheter according to various aspects of the present invention.

DETAILED DESCRIPTION OF THE INVENTION

Figure 1:
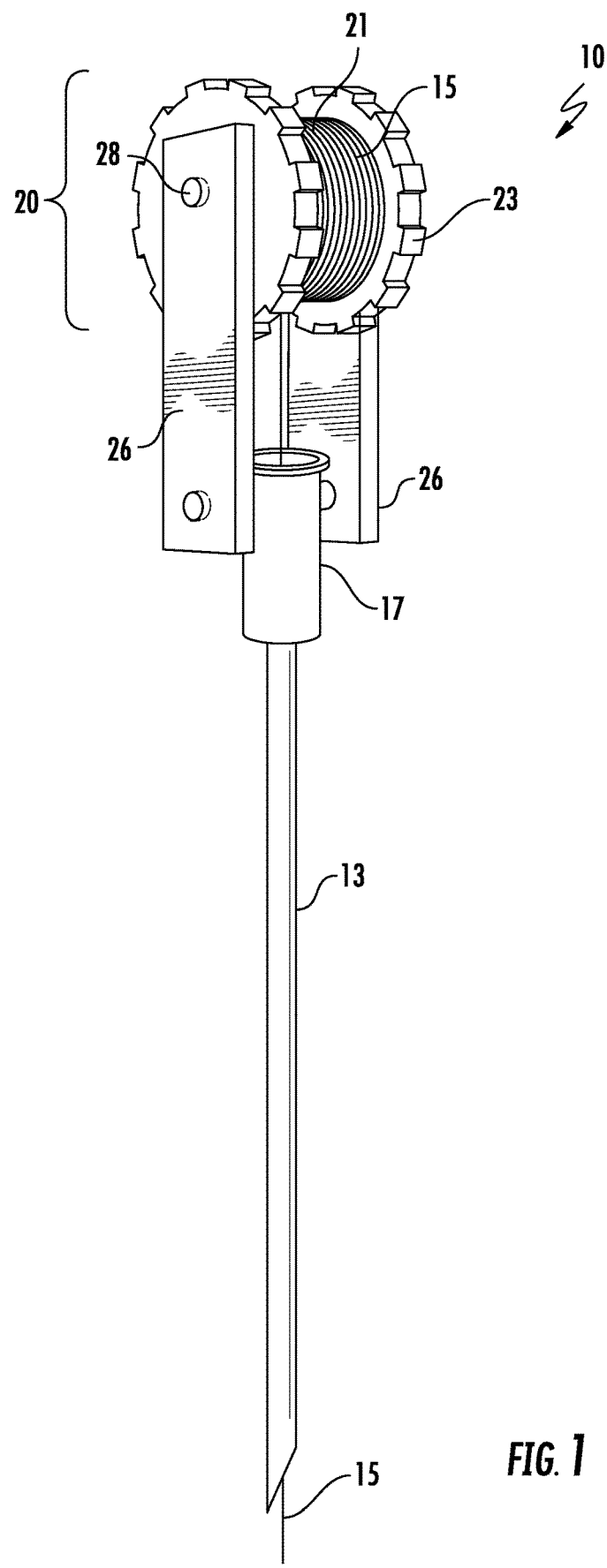
FIG. 1 is a perspective view of the spool assembly of the guidewire advancing device showing the guidewire.

The present invention will now be described in detail hereinafter by reference to the accompanying drawings. The invention is not intended to be limited to the embodiments described; rather, this detailed description is provided to enable any person skilled in the art to make and practice the invention.

The intravascular access assembly for use with a catheter includes the guidewire advancing device 10, a hollow needle 13, and a guidewire 15. The method according to the present invention includes the method of containing, advancing and guiding the wire distally to attain intravascular access. As used herein, the terms "proximal" and "distal" (excluding horizontal cross-sections) are used to refer to the axial ends of the assembly. The term "proximal end" refers to the end closely adjacent the user of the assembly and the term "distal end" refers to the end of the assembly to be intravascularly positioned.

For the purposes of its use with a rapid insertion venous catheter, the advancing device 10 is attached to the proximal end of the venous access needle 13 when the guidewire is preassembled within the needle. Alternatively, the guidewire may be inserted into the access needle during the procedure, that is, it is not "pre-loaded" into the needle. The device 10 may also be used in a manner as to be contained within the housing of a peripheral IV (PIV) or midline/extended dwell peripheral IV (EDPIV) device, or as a mechanism to be used in conjunction with any type and configuration of a peripheral or central line. One skilled in the art of vascular access and minimally invasive procedures could also envision a device that could contain this mechanism not only for peripheral or central venous access, but also for arterial access as is seen in arterial lines for invasive vital sign monitoring, or hemostatic vascular sheaths for venous/arterial procedures, for example. Additionally, the guidewire device 10 described herein could be used in conjunction or incorporated in a device used for percutaneous access into any cavity as is seen in image-guided drain/catheter placements into an abscess, the renal collecting system, biliary system, or any space or potential space of the human body.

According to one aspect of the present invention shown in FIGS. 1-7 and 19, the guidewire advancing device 10 of the present invention comprises a spool assembly 20 with the guidewire 15 coiled around the central portion 21. On either side are attached peripheral side members, such as, discs 23 that are larger than the spool 21 that serve to keep the guidewire 15 contained around the spool 21. The discs 23, are also used to rotate the spool assembly 20 and therefore may be notched on the surface for improved traction for the user's finger. The circumferential surfaces of the discs 23 provide the user interface for rotating the discs 23 to rotate the spool 21 and to drive the guidewire 15 along the length of the needle 13 and through its distal tip so as to extend within the vascular structure to be treated. The method of using the presently described invention includes positioning the needle 13 in the vascular structure to be treated, advancing the guidewire by rotating the one or both discs 23. The medical device, such as a catheter, to be intravascularly positioned may then be advanced over the guidewire until intravascular placement is achieved. The guidewire advancing device 10, needle 13 and guidewire 15 may then be removed, leaving the medical device intravascularly positioned. An interim step of verifying proper venous access and placement may also be conducted as described below.

Figure 2:
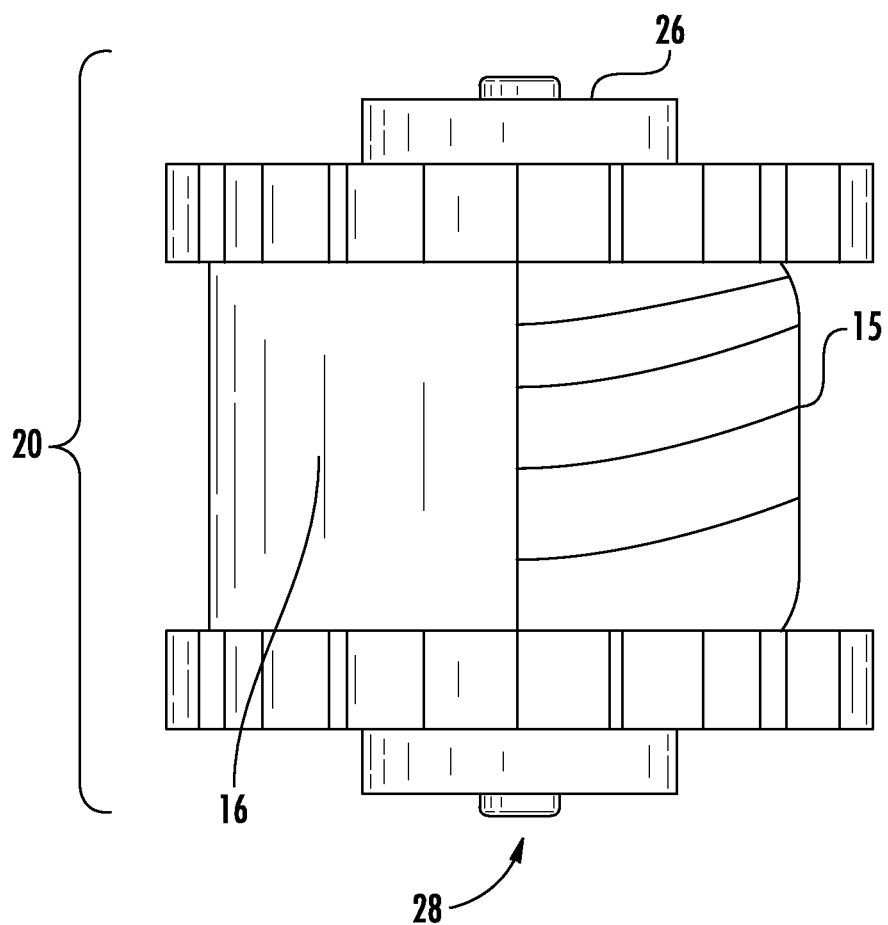
FIG. 2 is a top, perspective view of the spool assembly of FIG. 1.
Figure 3:
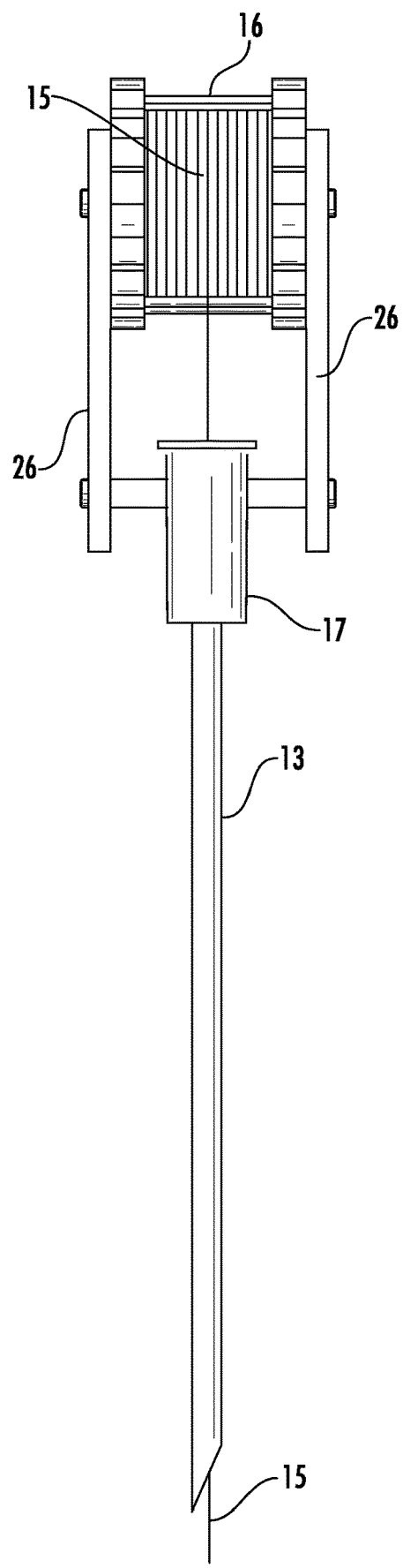
FIG. 3 is a front, perspective view of the spool assembly of FIG. 1.
Figure 4:
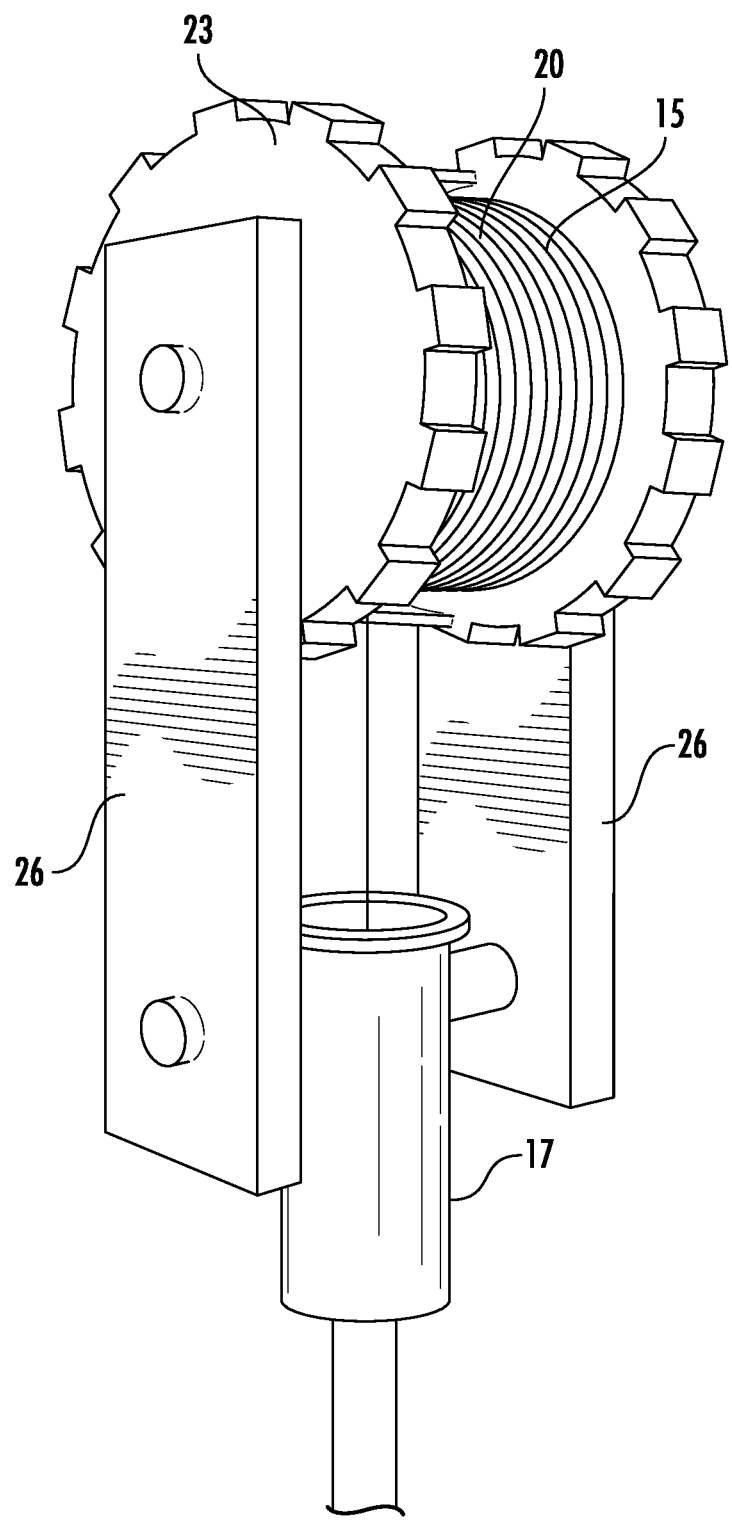
FIG. 4 is a perspective view of the spool assembly of the guidewire advancing device showing the guidewire advancing device in an operative position.
Figure 5:
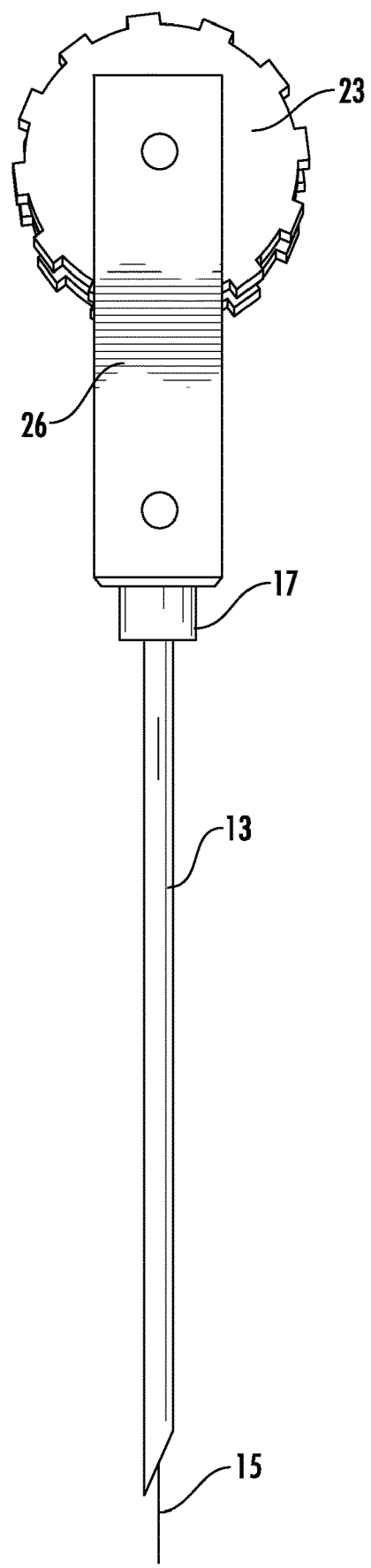
FIG. 5 is a side, perspective view of the spool assembly of FIG. 4 with the wire partially advanced for engagement.

The guidewire advancing device may also include a housing 16, shown in FIG. 2. The housing 16 is positioned between the discs 23 and extends around the spool 21 so as to surround the coiled guidewire 15 and defining a cavity or channel 24 therein for operative uncoiling of the wire 15. Housing 16 thereby contains the guidewire 15 and prevents unravelling as the spool 21 is being rotated to advance the guidewire 15. Supports 26 receive a shaft 28 which extends along and serves as the central axis of the spool 21. Supports 26 may alternatively be fixedly secured or removably secured to the needle hub 17 as described below.

Figure 6:
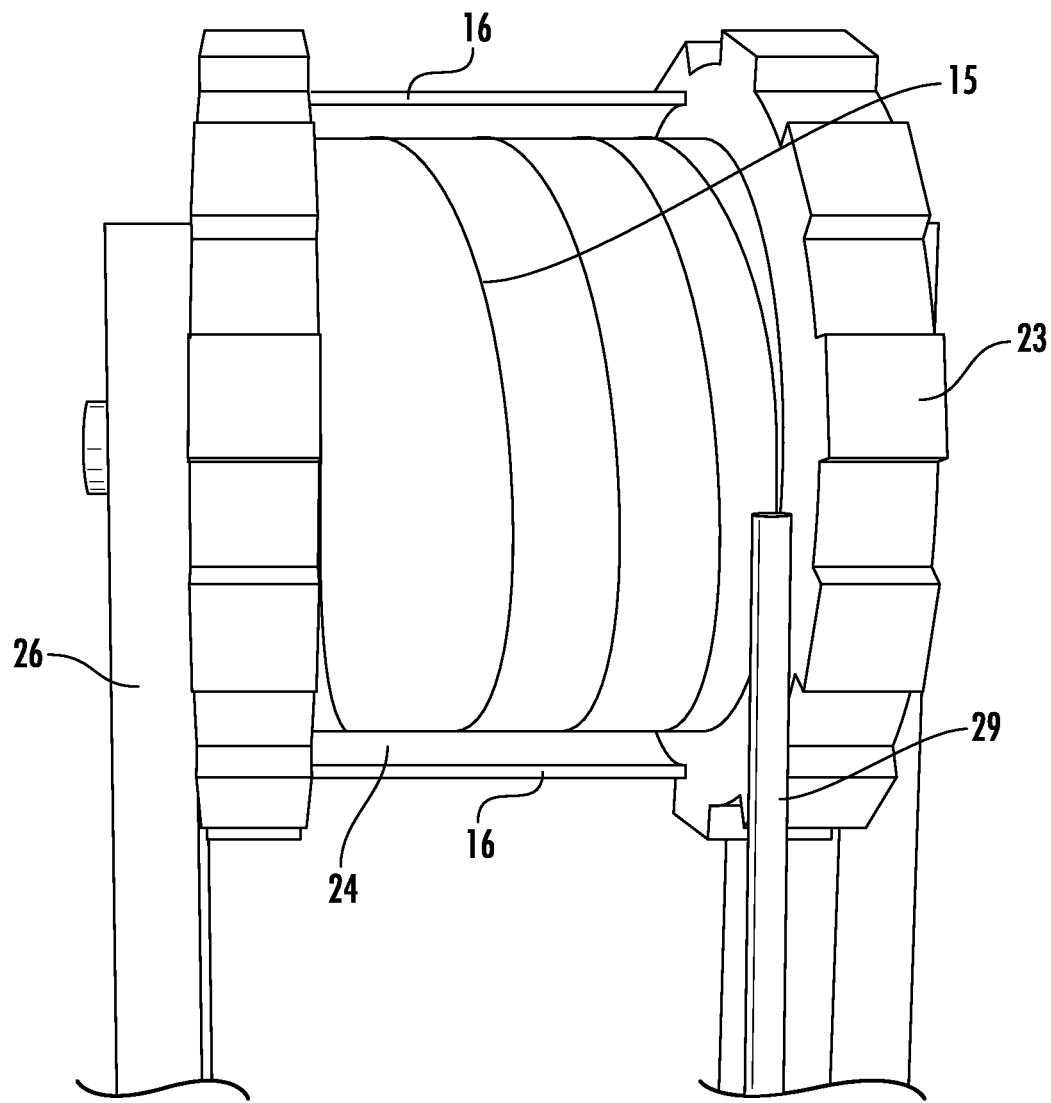
FIG. 6 is a front, perspective view of the spool assembly of FIG. 1.
Figure 7:
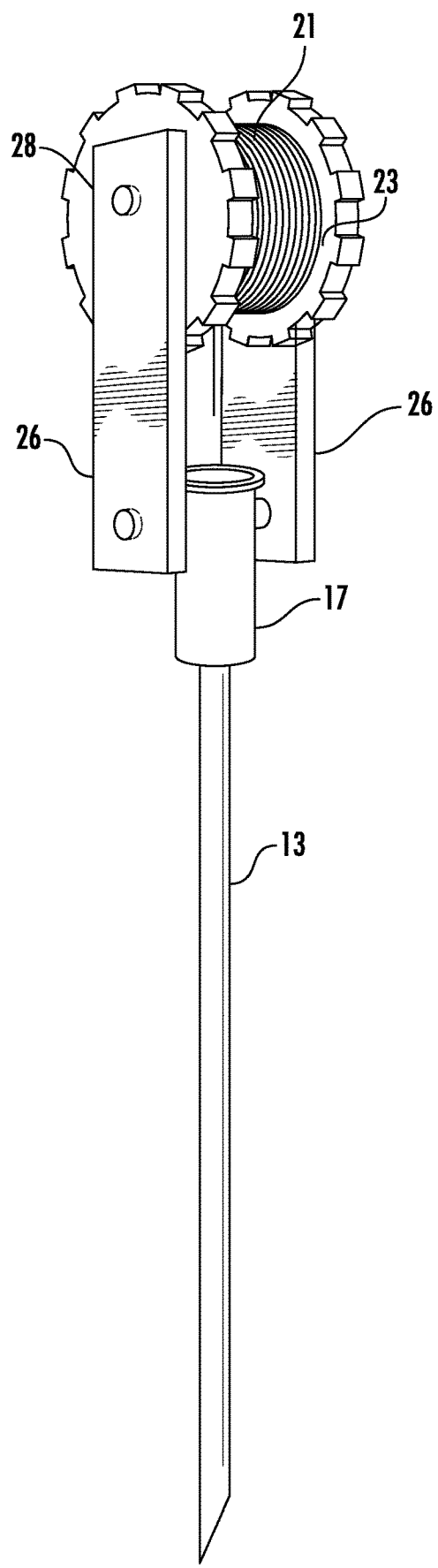
FIG. 7 is a perspective view of the spool device with the guidewire not advanced in the needle.

Preferably, channel 24 is in open communication with the proximal end of the needle 13 that when the device 10 is engaged (fixedly or removably) with the needle hub 17, the guidewire 15 may exit the cavity 24 and enter the hollow needle 13. As shown in FIG. 6, a guidewire guide 29 in the form of a hollow tubular member is provided to facilitate the extension of the guidewire 15 from the cavity 24 around the spool 21 and into the needle hub 17 and needle 13. This configuration directs the guidewire 15 into the needle 13 where it is then advanced longitudinally through the needle 13 and, hence, into the target vessel.

According to another aspect shown in FIGS. 19A and 19B, the guidewire advancing device 10 may be attached to the proximal end of the needle 13 in a moveable or hinged manner. This allows the device to be pivoted as shown in FIG. 19A wherein proximal access to the needle, as shown in FIG. 19B. As shown, the guidewire guide 29 is curvilinear and communicates directly with the proximal end of the needle 13 and needle hub 17. In the disengaged position, the advancing device 10 is rotated or otherwise moved away from the needle hub 17, allowing for use of a syringe or other device in conjunction with the access needle 13. This feature allows the user to confirm target vessel placement of the needle through aspiration of blood into a syringe. The syringe is then removed and the guidewire advancing device 10 is moved or rotated into the engaged position for advancing the guidewire 15 into the target vessel.

Figure 20A:
FIGS. 20A, 20B, and 20C are side elevational views of the guidewire advancing device of FIGS. 1-7 according to another aspect of the present invention.
Figure 20B:
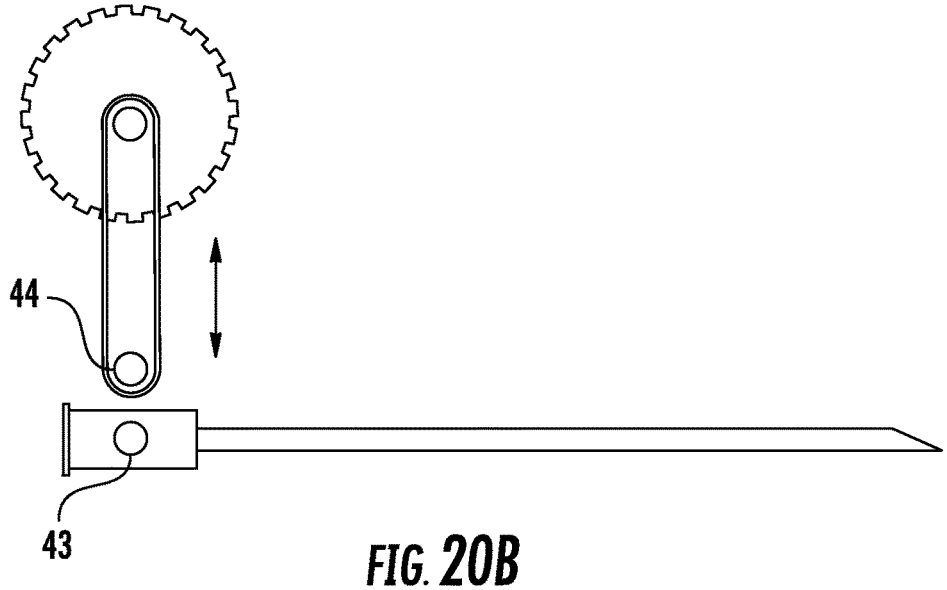
Figure 20C:
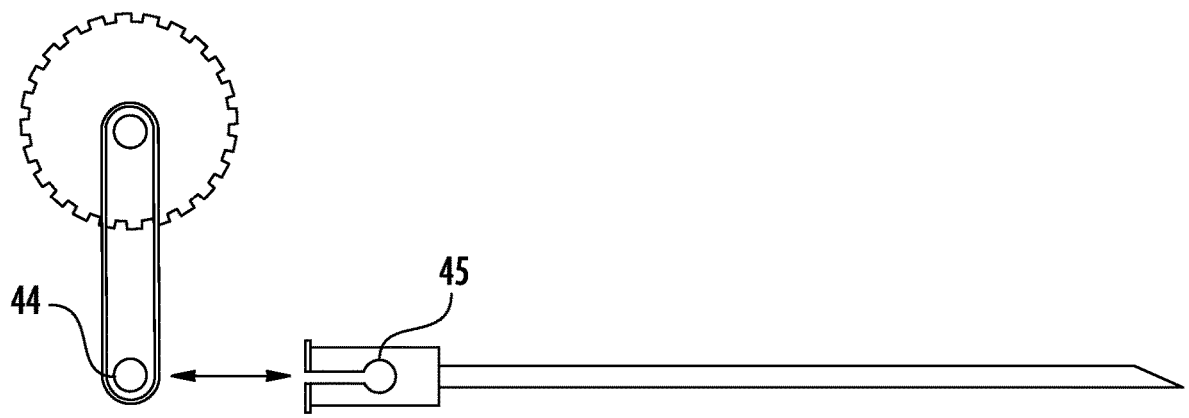

The spool assembly 20 may also be configured to be removable from the needle hub 17, whereby a semi-fixed, hinged connection existed provided between the needle hub 17 and the supports 26 as shown in FIGS. 20A, 20B and 20C. Inward facing posts 44, or other connections, are positioned on the distal ends of supports 26. Posts 44 connect to needle hub 17 though a focal recess 43, or alternatively, by a channel recess 45 to disengage by a snapping or sliding mechanism, respectively.

Figure 8:
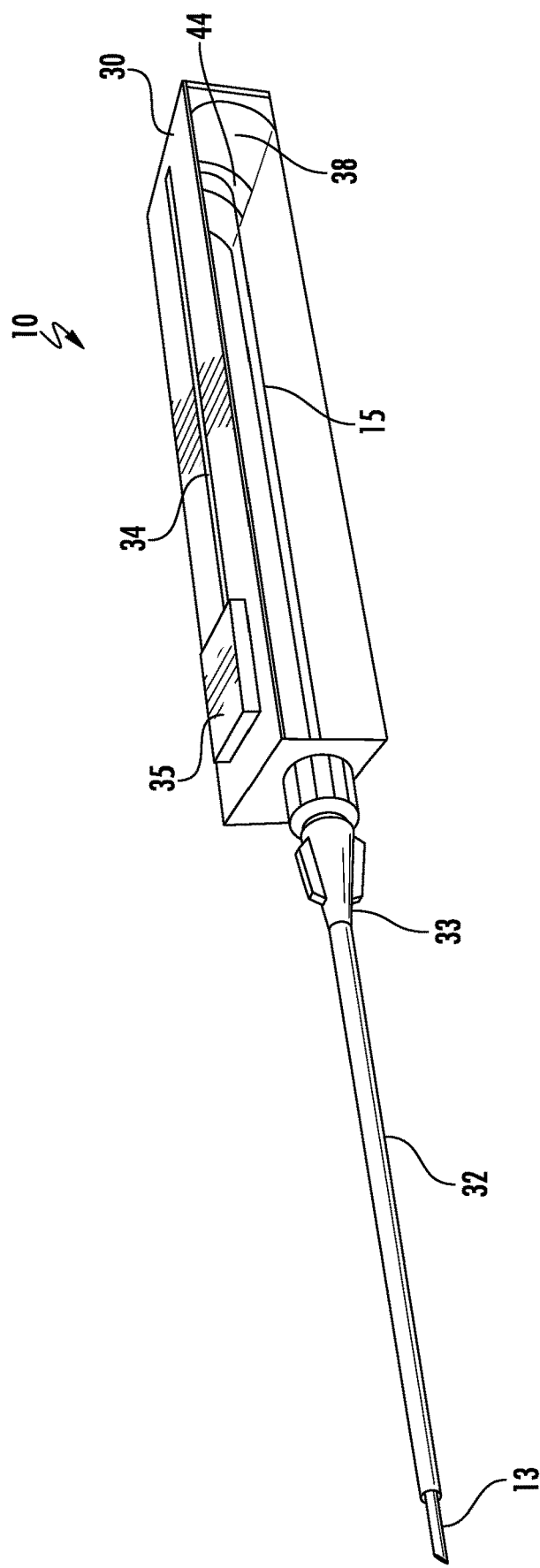
FIG. 8 is a perspective view of a guidewire advancing device according to another aspect of the present invention including an integrated device having a housing and a slide tab as the means for advancing the guidewire showing the sliding tab in a neutral or starting position.
Figure 9:
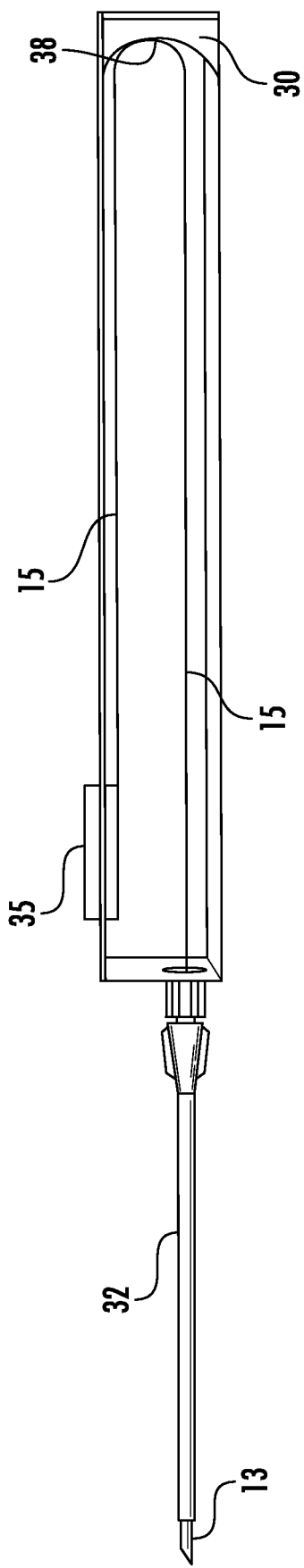
FIG. 9 is a side, elevational view, partially broken away, of the guidewire advancing device of FIG. 8.
Figure 10:
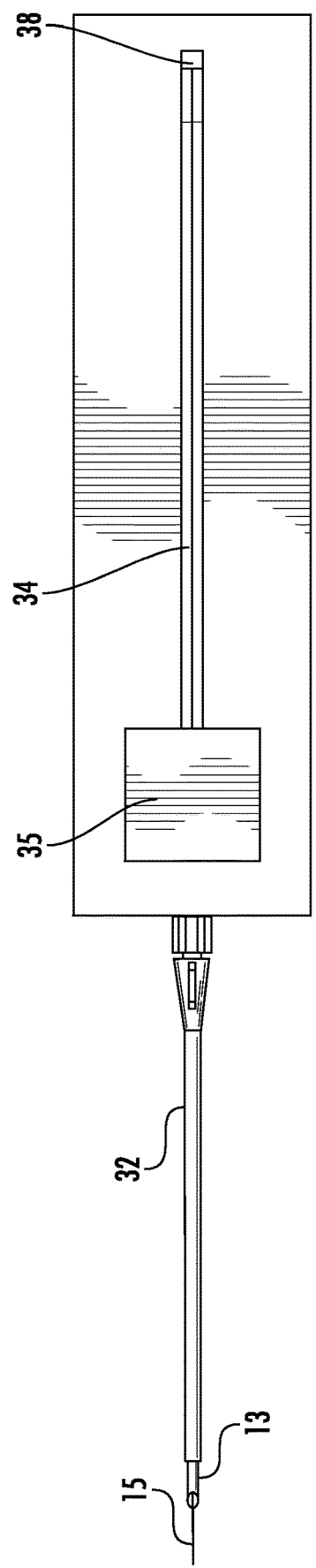
FIG. 10 is a top, plan view of the guidewire advancing device of FIG. 8 with the sliding tab in neutral or starting position.
Figure 11:
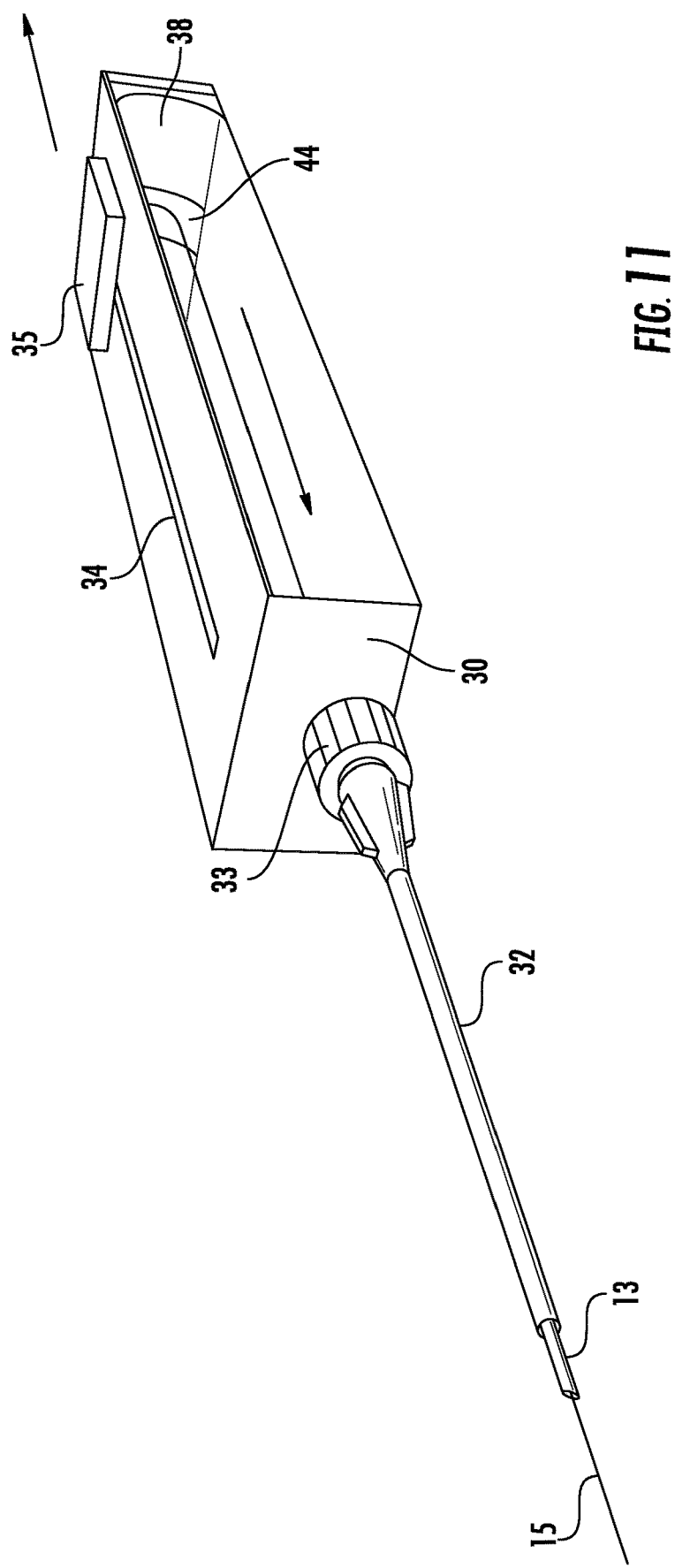
FIG. 11 is a perspective view of the guidewire advancing device of FIG. 8 with the sliding tab in an engaged, fully extended position.

According to another aspect of the present invention, the guidewire advancing device 10, as shown in FIGS. 8-12, includes different means for advancing the guidewire 15. As shown, the guidewire advancing device 10 is an integrated catheter assembly and includes a generally rectangular housing 30 configured to cooperate with the needle 13. As shown in FIG. 8, a catheter 32 is shown housing the needle 13 and a catheter hub 33 is provided as an interface between the housing 30 and catheter 32. The housing 30 defines a longitudinally extending channel 34 configured for receipt of a tab 35. Tab 35 is configured to slidably move along the length of the channel 34. The housing 30 and tab 35 are shown as generally rectangular, but any ergonomic configuration may be selected. Also, the channel 34 may be positioned on any wall of the housing 30, e.g., a side wall.

Figure 12:
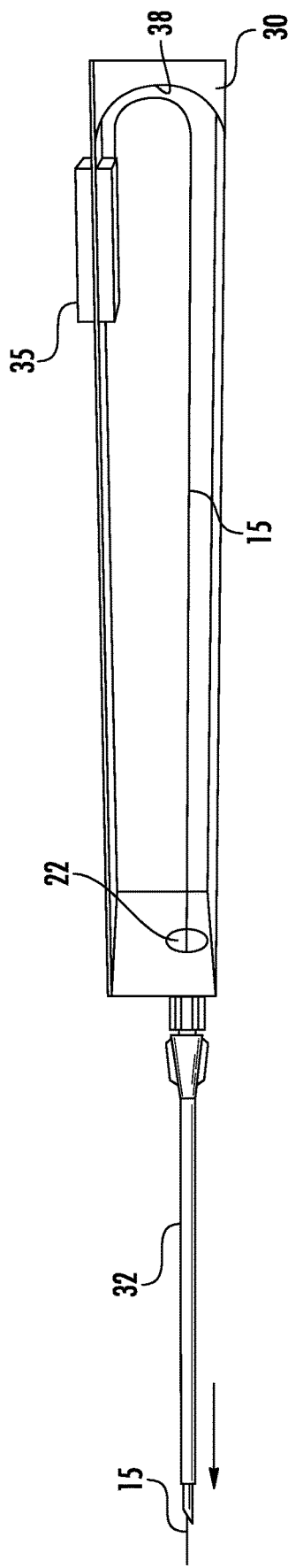
FIG. 12 is a side elevational view of the guidewire advancing device in the position of FIG. 11.
Figure 13:
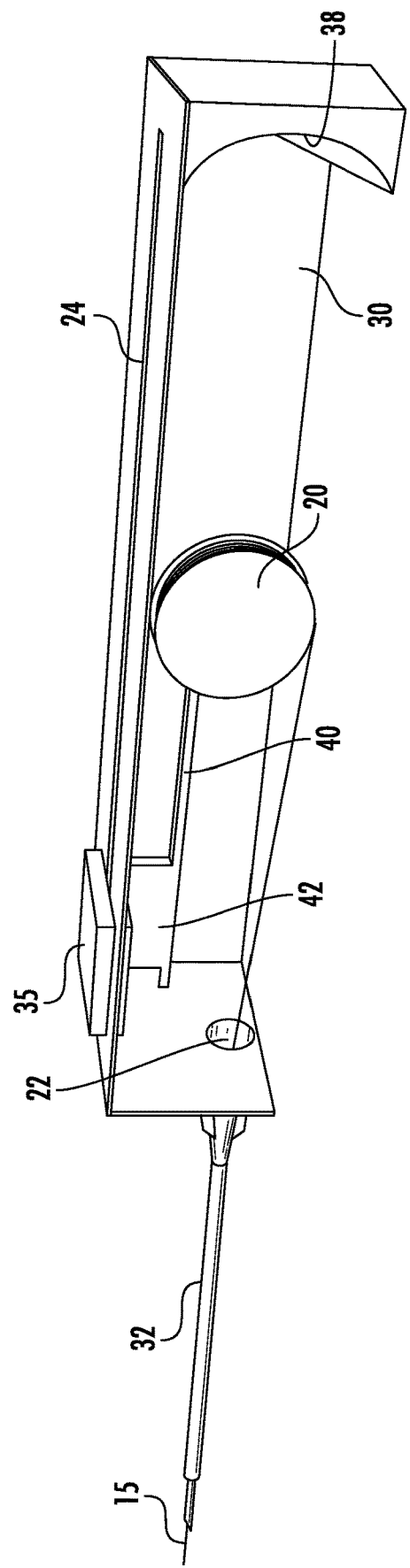
FIG. 13 is side, perspective view, partially broken away, of the guidewire advancing device having a slide tab as shown in FIGS. 8-12 for advancing the guidewire and gear assembly for operatively transferring forces applied to the slide tab to the guidewire.
Figure 14:
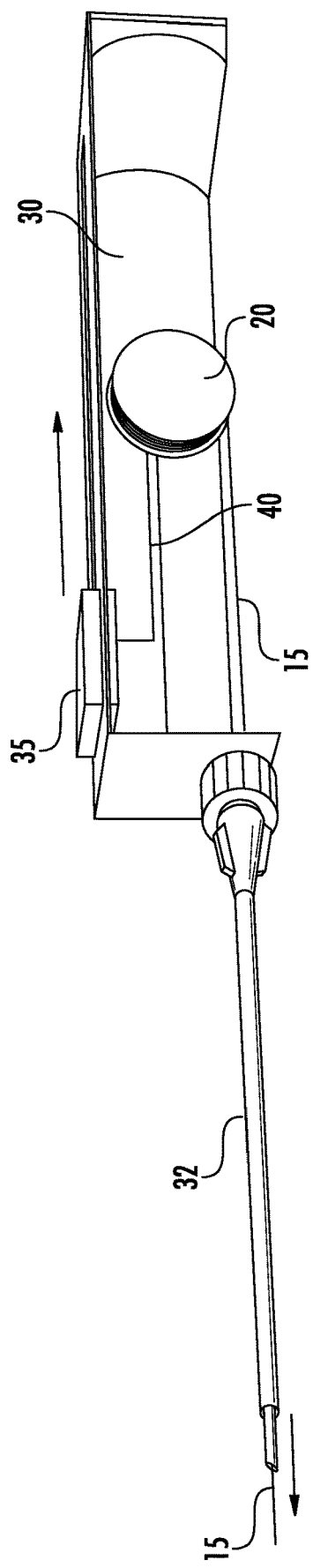
FIG. 14 is a perspective view, partially broken away, of the guidewire advancing device of FIG. 13 with the guidewire positioned for engagement.
Figure 15:
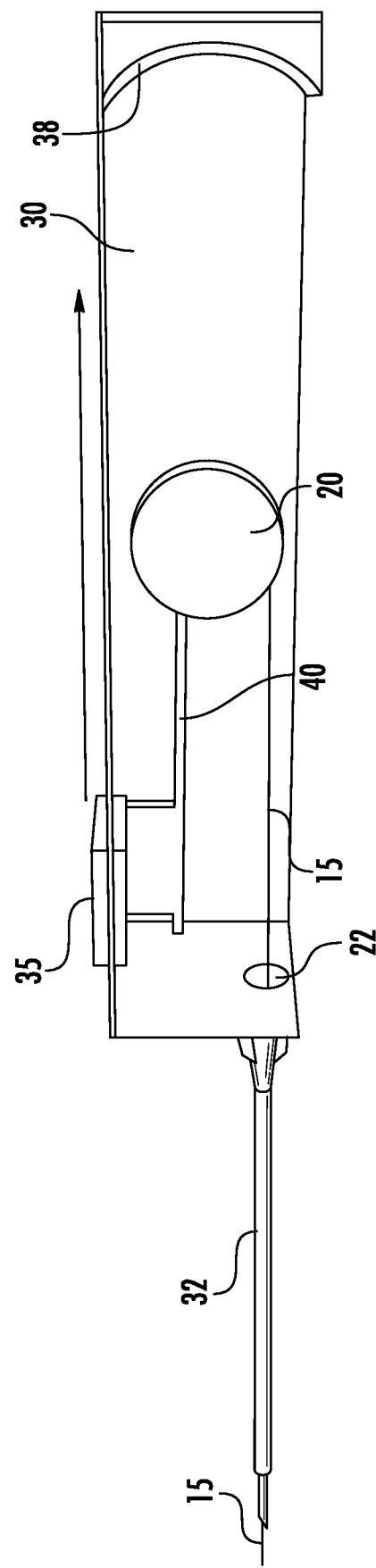
FIG. 15 is a side, elevational view, partially broken away, of the guidewire advancing device of FIG. 13.
Figure 16:
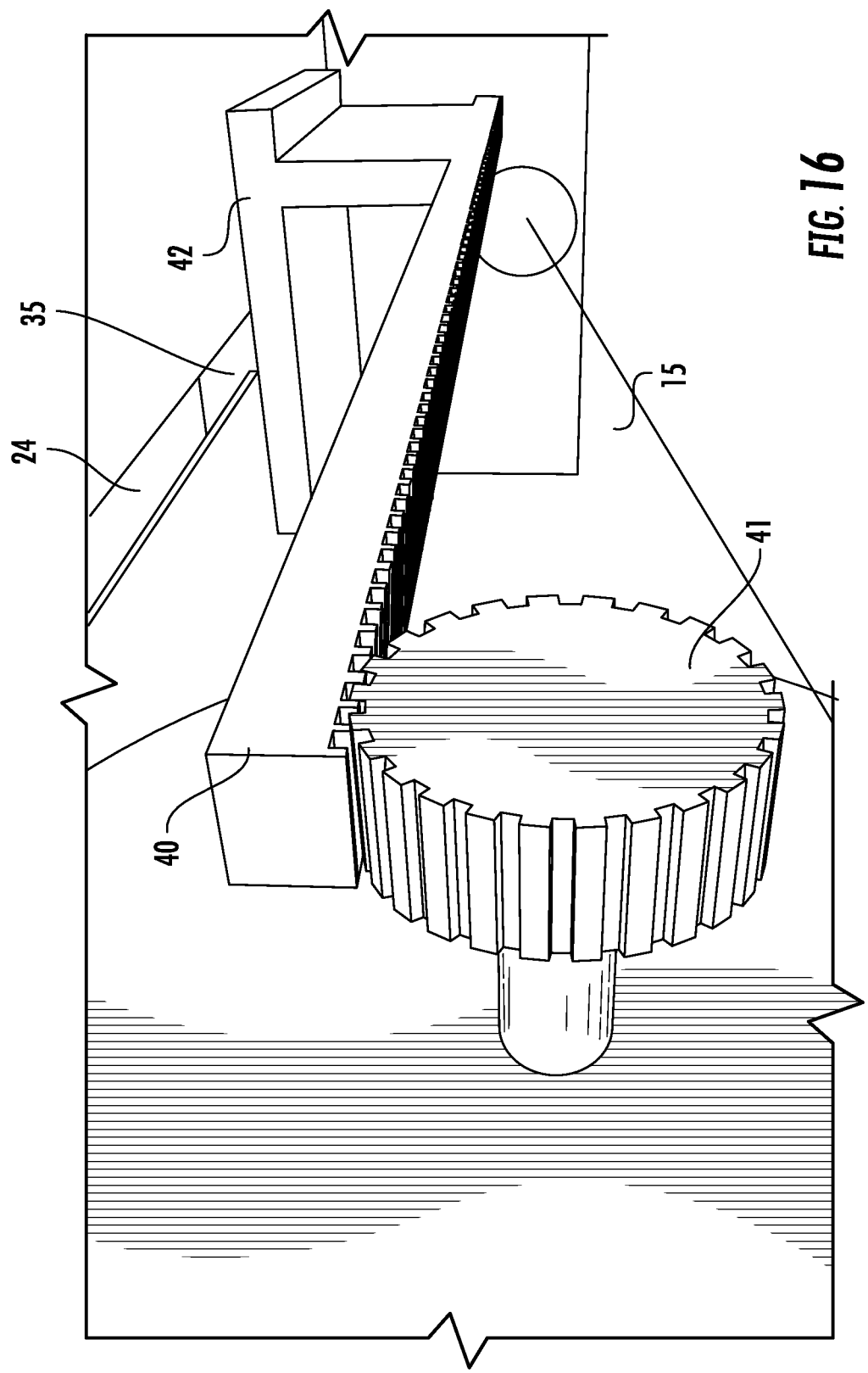
FIG. 16 is an enlarged, interior view of the guidewire advancing device of FIG. 13.

Within the housing 30, the sliding tab 35 is connected to the proximal end of the guidewire 15. The slide tab 35 includes an exterior member for engagement by the user and an interior member coupled to the guidewire 15. The guidewire 15 extends proximally from the slide tab 15 along an upper, interior surface of the housing 30 and curves around a proximal rear surface of the housing 30 so as to change direction and extend distally toward the needle 13. Preferably, a guide channel 44 is provided to facilitate smooth movement of the wire 15 within the housing 16. As shown in FIGS. 8 and 12, a wire deflecting curve 38 is defined by the rear proximal surface of the housing 16. Accordingly, the user may slide the tab 35 in the proximal direction to advance the guidewire into the needle 13 for vascular placement while advancing the guidewire 15 distally.

In the starting position, when the needle is not pre-assembled with the guidewire, the guidewire tip is proximal to the proximal end of the access needle 13. This allows the user to visualize a flash of blood when the needle tip punctures the vessel. Alternatively, the wire 15 may be pre-loaded into the proximal end of the needle, and other various methods of confirming intravascular needle placement may be employed. An example of such blood flashback mechanism is U.S. Pat. No. 5,295,970 to Clinton et al. To advance the wire into (if not pre-engaged) and longitudinally through the needle, the sliding tab 35 is advanced proximally along the channel 34 within the housing 30. This action advances the wire 15 along its channel within the housing 30 and into the needle 13 so as to advance along its length and into the target vessel.

According to the present invention, the operator's finger is already touching and engaged with the tab 35 while advancing the needle into the desired vessel. Therefore, the operator does not need to move his/her finger, or require the use of the other hand/finger, to re-engage a more proximally placed tab starting position. This is a favorable configuration since the wire placement is truly single-handed and reduces risk of dislodging the needle or wire while trying to locate and manipulate a more proximally placed tab.

In the aforementioned aspects of the present invention, a gear assembly, in the form of a rack 40 and gear wheel or pinion 41, may be incorporated into the guidewire advancement device 10 as shown in FIGS. 13-18. As shown, the rack 40 and gear 41 are coupled to the slide tab 35 and to the guidewire 15 (with or without an intermediate spool assembly 20). The gear assembly provides the guidewire 15 with greater translation of forces as it exits the needle tip into the desired vessel with a respectively smaller movement of the engaging user's finger. The tab 35, best shown in FIG. 16, includes an intermediate arm 42 extending from the slide tab 35 interior member which is coupled to the rack 40. A bottom surface of the rack 40 defines a plurality of teeth configured to cooperate with the teeth of the gear 41 for which it cooperates. Thus, when the slide tab 35 is slid proximally, the rack 40 also moves proximally because they are rigidly connected. The gear configuration facilitates rotation of the spool 21 to advance the guidewire for insertion into the needle 13 for vascular access. If used in connection with a spool assembly 20 as in FIGS. 1-7, the shaft of the gear 41 is coupled to the spool 21. The size ratio between the gear 41 and spool 21 dictates how much guidewire 15 is advanced with movement of the tab 35. This feature allows a greater amount of guidewire 15 to be advanced per unit length of movement of the tab 35. For example, an amount of guidewire 15 equal to two times or three times the distance of travel of the tab 35 can be advanced into the vessel. Although the current description has the teeth on the lower surface of the rack to communicate with the gear, it is within the scope of the invention to have the teeth on the upper or side surfaces of the rack with an appropriate corresponding configuration of the gear.

Figure 17:
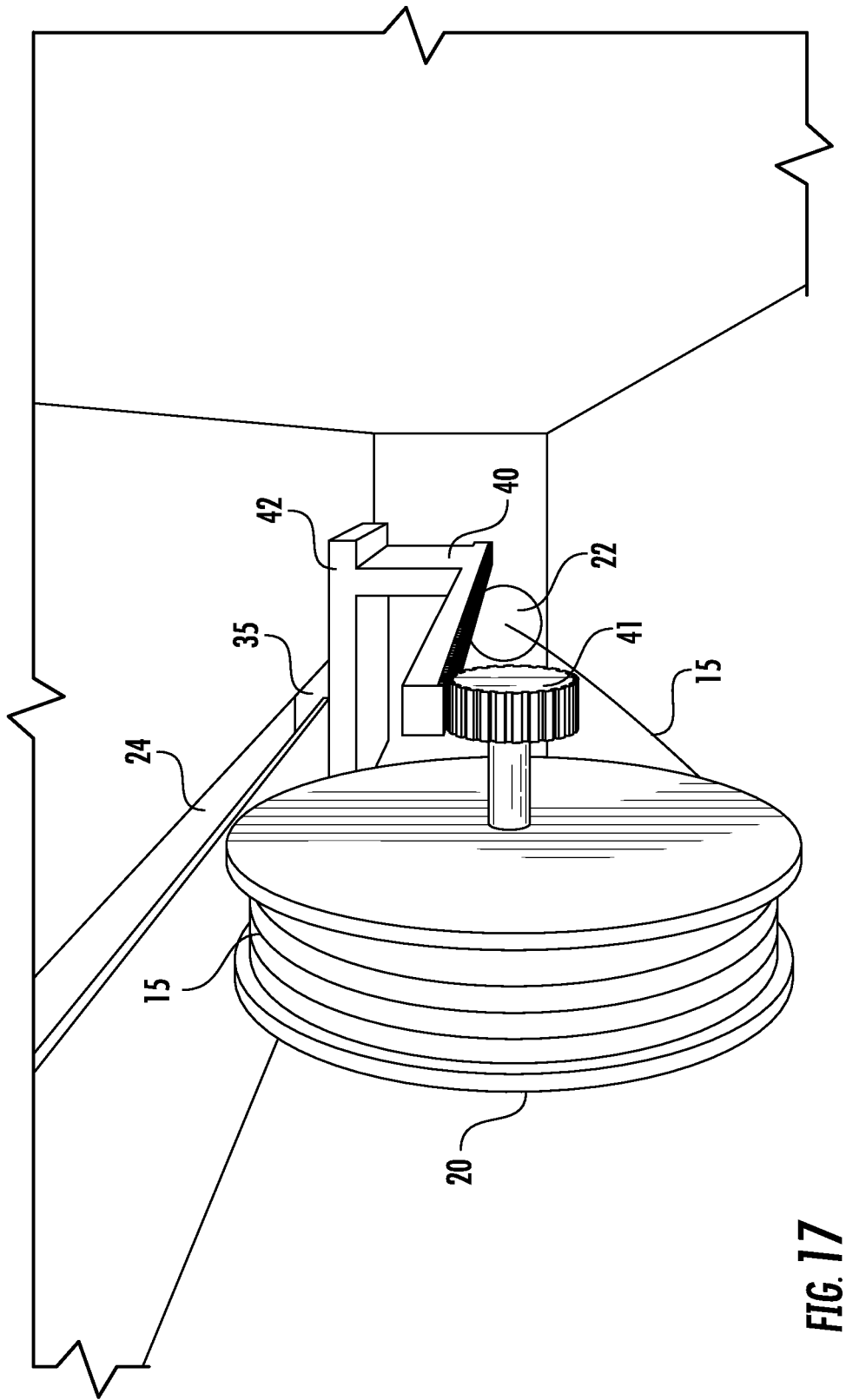
FIG. 17 is an enlarged, interior and partially broken away view of the guidewire advancing device including a spool as the means for advancing the guidewire of FIGS. 1-7 and an integrated catheter of FIGS. 8-12 and a gear assembly for coupling the spool to the guidewire.
Figure 18:
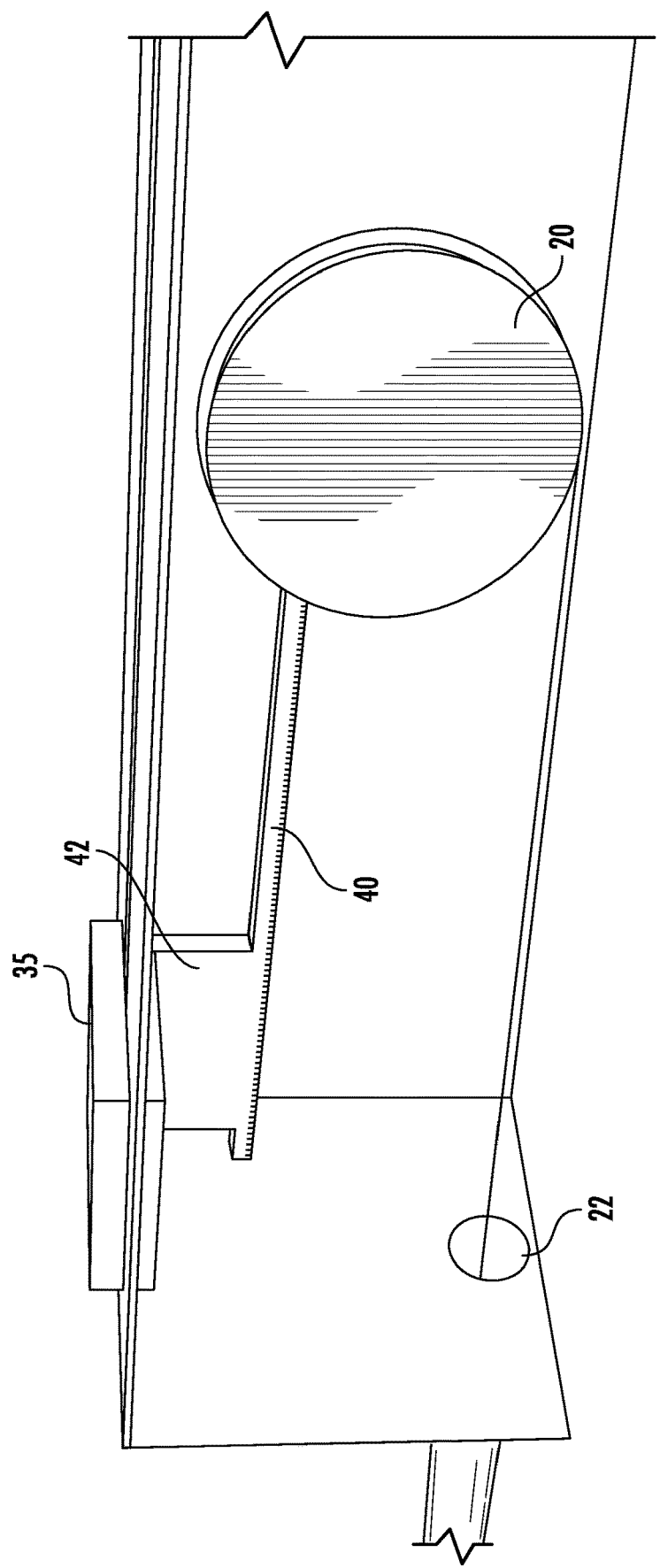
FIG. 18 is an enlarged, partially broken away, side perspective view of the guidewire advancing device including a slide tab as the means for advancing the guidewire of FIGS. 8-12 and a gear assembly for coupling the spool to the guidewire.

Another aspect of the present invention is shown in FIG. 17 which includes the slide tab 35 as described above with regard to FIGS. 8-12, a spool assembly 20 as described above with regard to FIGS. 1-7, and a gear assembly described with regard to FIGS. 13-16, 18. As shown, the spool assembly 20 includes the pinion gear 41 for cooperating with the rack 40 coupled to the slide tab 35.

In all configurations, the wire comprises a metallic material that first has a relatively soft, floppy distal end that enters the vessel, followed by stiffer solid core wire portion. Although many metallic materials could be used, such as stainless steel, the preferred material for most applications would be that of a non-deformable metallic alloy such as nitinol. Additionally, it should be noted that if a wire guide is used as seen in one alternative embodiment, the transition of soft and stiff portions of the wire would need to be contained within. Alternatively, if no wire guide was used and the wire was pre-engaged in the needle, the transition portion of the wire would also need to be contained within the needle to facilitate distal advancement.

In all configurations, the proximal aspect of the guidewire is preferably attached to the advancing device, preventing loss of the guidewire through the needle and into the target vessel as this can be a catastrophic event requiring surgical or endovascular removal or snaring, respectively, of the guidewire.

The method of using the novel guidewire advancing device according to the presently described aspects includes the following. Once the skin surface is prepped and draped in the usual sterile manner, the targeted vessel is accessed by means of direct visualization, palpation, or imaging guidance, or a combination thereof. Upon obtaining access with the distal tip of the needle 13 into the desired vessel, confirmation of needle tip location may be performed by methods standard in the art (i.e. visual confirmation with ultrasound or blood via a blood flashback mechanism, amongst other methodologies). When the operator has sufficiently demonstrated an appropriate intravascular location of the needle tip, the guidewire advancing device 10 is engaged. According to one aspect, the guidewire 15 is preloaded in the needle 13 lumen, and readily available for intravascular advancement. The user engages the tab 35 with a finger and begins to deploy the guidewire 15. The guidewire is advanced distally by proximal linear movement of the tab 35 which is connected to the rack 40. The rack's 40 linear motion thereby rotates the gear 41 which is connected to the spool assembly 20. Rotation of the gear 41 and spool 21 unwinds the guidewire 15 from the spool, advancing the guidewire 15 through the needle 13 and into the target vessel. The finger may be engaged with the tab 35 in the distal starting position, as shown, or may engage a tab 35 in a more proximal location. Ultimately, significantly greater travel of guidewire is then achieved at some predetermined multiple to a relatively smaller movement of the operator's finger.

Once the catheter 12 is distally advanced over the needle 13 and guidewire 15, the guidewire advancing device 10 is removed with the needle 13 and guidewire 15. One or more safety mechanisms and blood containment devices would preferably be employed for best practice removal of vascular access needles to prevent blood spillage, contamination, and transmission of potential blood-borne infections.

While exemplary embodiments have been shown and described above for the purpose of disclosure, modifications to the disclosed embodiments may occur to those skilled in the art. The disclosure, therefore, is not limited to the above precise embodiments and that changes may be made without departing from its spirit and scope.

What is claimed is:

1. A guidewire advancing device comprising:
   a guide wire;
   a hollow needle wherein the needle is configured for receipt within a lumen of a catheter, the needle having a proximal end and a distal end for medical device placement and access into an anatomical structure said guidewire configured for receipt along the length of the hollow needle so as to be inserted into said needle proximal end to selectively extend from said needle distal end; and
   an advancing assembly for initially supporting said guidewire and for selectively advancing a portion of said guidewire distally through the needle proximal end and beyond the needle distal end, said advancing assembly comprising a spool rotatably supported on a shaft for receiving a proximal portion of said guidewire initially being wound on said spool, at least one peripheral member coupled to said spool and rotatably mounted on said shaft wherein said at least one peripheral member is coupled to said spool and includes an outer surface configured for user interface for rotating said peripheral member wherein movement of said at least one peripheral member rotates said spool about said shaft to advance the distal end of said guidewire distally wherein said advancing assembly is operatively connected to said needle proximal end;
   wherein the advancing assembly is hingedly connected to the needle so as to pivot said advancing assembly about a longitudinal axis of the needle.

2. A guidewire advancing device according to claim 1 wherein said hollow needle initially houses a distal portion of the guidewire and which extends distally from said advancing assembly.

3. A guidewire advancing device according to claim 2 further comprising a needle hub connected to the proximal end of said needle and said needle hub is coupled to said advancing assembly.

4. A guidewire advancing device according to claim 1 further comprising a longitudinally extending guidewire guide having a proximal and distal end wherein said guidewire is advanced from said advancing assembly, through said proximal and distal end of said guidewire guide and through said needle.

5. A guidewire advancing device according to claim 1 further comprising a guidewire housing extending along a circumferential outer surface of said spool so as to define a circumferentially extending channel for housing said guidewire.

6. A guidewire advancing device according to claim 5 wherein said housing substantially encloses a portion of said spool and defines an aperture for advancement of said guidewire.

7. A guidewire advancing device according to claim 1 wherein said advancing assembly includes a support is connected to said shaft of said spool.

8. A guidewire advancing device according to claim 1 wherein said outer surface of said at least one peripheral member includes at least one notch.

9. A guidewire advancing device according to claim 1 comprising wherein the advancing assembly comprises at least one support extending between said spool and said needle for securing said spool to the proximal end of the needle.

10. A guidewire advancing device according to claim 9 wherein said at least one support is connected to a needle hub of said needle.

11. A guidewire advancing device according to claim 10 wherein said at least one support is removably connected to said needle hub.

12. A guidewire advancing device according to claim 11 wherein said needle hub defines an aperture and said at least one support includes a post configured for receipt within said needle hub aperture for removing said advancing assembly from said needle.

13. A guidewire advancing device according to claim 12 wherein said aperture is a channel.

14. A guidewire advancing device according to claim 1 wherein said advancing assembly comprises two peripheral members on opposing sides of said spool.

15. A guidewire advancing device comprising:
    a catheter for placement into the anatomical structure having a proximal and distal end and a longitudinal length therebetween;

a needle extending along the longitudinal length of the catheter;

a housing configured to cooperate with and be operatively associated with the catheter proximal end and the needle, said housing having a predetermined length extending between proximal and distal ends thereof and having an upper surface and proximal and distal end surfaces;

a channel defined by said housing surfaces and extending a predetermined distance between said proximal and distal ends of said housing;

a tab slidably positioned within said channel so as to move along the length of the channel;

a guidewire having a proximal and distal end, said guidewire proximal end being coupled to said tab and said guidewire distal end extending outwardly from said housing distal end and within said catheter and needle;

a proximal end surface defined by said housing configured to alter the direction of said guidewire when said tab is moved proximally so as to advance the guidewire distally to extend within an anatomical structure being treated.

16. A guidewire advancing device according to claim 15 wherein said tab comprises an exterior member configured to manual operation which extends outwardly from said channel and an interior member wherein said guidewire is connected to said interior member.

17. A guidewire advancing device according to claim 15 wherein said upper surface of said housing defines said channel.

18. A guidewire advancing device according to claim 15 wherein said proximal end surface is a curved surface having a predefined arc defined by said housing proximal end.

19. A guidewire advancing device according to claim 15 wherein said tab is connected to said guidewire and is moved proximally to advance the guidewire distally.

20. A guidewire advancing device comprising:
a catheter for placement into the anatomical structure having a proximal and distal end and a longitudinal length therebetween;

a needle extending along the longitudinal length of the catheter;

a housing configured to cooperate with and be operatively associated with the catheter proximal end and the needle, said housing having a predetermined length extending between proximal and distal ends thereof and having an upper surface and proximal and distal end surfaces;

a channel defined by at least one of said housing surfaces and extending a predetermined distance between said proximal and distal ends of said housing;

a tab slidably positioned within said channel so as to move along the length of the channel;

a guidewire having a proximal and distal end, said guidewire proximal end being connected to said tab and said guidewire distal end extending outwardly from said housing distal end and within said catheter and needle;

a rack coupled to the slide tab, said rack having a mating surface, and a gear having an outer surface configured to mate with said mating surface and a spool positioned within said housing and rotatably supported on a shaft for receiving a proximal end and a proximal portion of said guidewire wherein said spool is coupled to the said gear and rotates when said gear rotates to advance said guidewire.

21. A guidewire advancing device according to claim 20 wherein said tab comprises an exterior member configured to manual operation which extends outwardly from said housing channel and an interior member wherein said guidewire is connected to said interior member.

22. A guidewire advancing device according to claim 20 wherein said upper surface of said housing defines said channel.

23. A guidewire advancing device according to claim 20 wherein said guide channel is a curved surface having a predefined arc defined by said housing proximal end.

24. A guidewire advancing device according to claim 20 wherein said tab is coupled to an intermediate arm and said intermediate arm is coupled to said rack.

25. A guidewire advancing device according to claim 20 wherein said shaft connected to said housing.

26. A method of placing a guidewire advancing device comprising the steps of:
providing a guidewire extending along the length of a hollow needle having a proximal and distal end so as to be inserted into said needle proximal end to selectively extend from said needle distal end;

providing an advancing assembly and supporting the advancing assembly on a proximal end of the needle and comprising a spool rotatably supported on a shaft and a peripheral member coupled to the spool and rotatably supported on the shaft, the spool initially supporting a proximal portion of said guidewire which is wound on the spool, wherein said advancing assembly is hingedly connected to the needle so as to pivot the advancing assembly about a longitudinal axis of the needle;

inserting the needle within the vascular structure to be treated;

rotating said peripheral member by interfacing with an outer surface thereof so as to rotate the peripheral member and the spool about the same shaft and selectively advancing a distal portion of said guidewire distally through the needle proximal end and beyond the needle distal end; advancing a catheter over the guidewire to achieve vascular access with the catheter.

27. A method according to claim 26 further comprising the steps of providing a peripheral member connected to the spool and supported on the shaft and rotating said peripheral member about said shaft and rotating said spool.

28. A method of placing an integrated guidewire advancing device including a catheter operatively connected to a housing, a needle extending along a length of the catheter, a guidewire extending within a lumen of the needle comprising the steps of:
providing a housing having a predetermined length extending between proximal and distal ends thereof and having an upper surface and proximal and distal end surfaces, a channel defined by a housing surface and extending a predetermined distance between said proximal and distal ends of said housing, and a tab slidable positioned within said channel so as to move along the length of the channel and the housing defines a proximal end surface wherein the guidewire extends from the tab proximally and cooperates with the proximal end surface to alter direction and extend distally;

inserting the needle within the target vessel to be treated;

sliding the tab within the channel proximally;

altering the direction of guidewire travel and distally advancing the guidewire from the needle distal end and into the target vessel;

advancing the catheter over the guidewire to achieve vascular access with the catheter; and removing the catheter, needle and guidewire as an integrated unit.

29. A method of placing an integrated guidewire advancing device including a catheter operatively connected to a housing, a needle extending along a length of the catheter, a guidewire extending with a lumen of the needle comprising the steps of:

providing a housing having a predetermined length extending between proximal and distal ends thereof and having an upper surface and proximal and distal end surfaces, a channel defined by a housing surface and extending a predetermined distance between said proximal and distal ends of said housing, and a tab slidably positioned within said channel so as to move along the length of the channel;

supporting the guidewire on a rotatable spool within the housing;

inserting the needle within a target vessel to be treated;

sliding the tab within the channel proximally, engaging a rack with said tab;

rotating a gear operatively engaging said rack and rotating the spool to dispense the guidewire;

advancing the guidewire distally to achieve vascular access; and removing the catheter, needle and guidewire as an integrated unit.

* * * * *